(12) United States Patent
Powers et al.

(10) Patent No.: US 6,762,137 B2
(45) Date of Patent: Jul. 13, 2004

(54) WATER REPELLANT MELTBLOWN WEBS AND LAMINATES

(75) Inventors: Michael D. Powers, Canton, GA (US); Steven W. Fitting, Acworth, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 125 days.

(21) Appl. No.: 10/025,377

(22) Filed: Dec. 19, 2001

(65) Prior Publication Data

US 2002/0142691 A1 Oct. 3, 2002

Related U.S. Application Data

(60) Provisional application No. 60/257,229, filed on Dec. 21, 2000.

(51) Int. Cl.[7] .................... B32B 27/02; B32B 27/04; B32B 5/26; D04H 1/56; D04H 3/16
(52) U.S. Cl. .................... 442/79; 442/170; 442/171; 442/382; 442/400; 442/401; 442/414; 428/375
(58) Field of Search .................... 442/79, 82, 170, 442/171, 382, 400, 401, 414; 428/364, 365, 375

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Peterson |
| 3,502,763 A | 3/1970 | Hartman |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,041,203 A | 8/1977 | Brock et al. |
| 4,340,563 A | 7/1982 | Appel et al. |
| 4,655,760 A | 4/1987 | Morman et al. |
| 4,657,802 A | 4/1987 | Morman |
| 4,720,415 A | 1/1988 | Vander Wielen et al. |
| 4,766,029 A | 8/1988 | Brock et al. |
| 4,781,966 A | 11/1988 | Taylor |
| 4,789,699 A | 12/1988 | Keiffer et al. |
| 4,965,000 A | 10/1990 | Potts et al. |
| 4,965,122 A | 10/1990 | Morman |
| 4,981,747 A | 1/1991 | Morman |
| 5,169,706 A | 12/1992 | Collier, IV et al. |
| 5,178,931 A | 1/1993 | Perkins et al. |
| 5,178,932 A | 1/1993 | Perkins et al. |
| 5,188,885 A | 2/1993 | Timmons et al. |
| 5,226,992 A | 7/1993 | Morman |
| 5,336,545 A | 8/1994 | Morman |
| 5,382,400 A | 1/1995 | Pike et al. |
| 5,464,688 A | 11/1995 | Timmon et al. |
| 5,607,798 A | 3/1997 | Kobylivker et al. |
| 6,586,522 B1 * | 7/2003 | Jariwala et al. ............. 524/539 |

FOREIGN PATENT DOCUMENTS

| | | |
|---|---|---|
| EP | 0761846 A3 | 3/1997 |
| WO | WO 9325746 | 12/1993 |
| WO | WO 9515848 | 6/1995 |

OTHER PUBLICATIONS

International Search Report dated Dec. 21, 2001.

* cited by examiner

Primary Examiner—Cheryl A. Juska
Assistant Examiner—Jenna-Leigh Befumo
(74) Attorney, Agent, or Firm—Dority & Manning, P.A.

(57) ABSTRACT

Nonwoven webs with good barrier properties are disclosed. The nonwoven webs can be, for instance, meltspun webs such as meltblown webs and spunbonded webs. In accordance with the present invention, a hydrophobic agent is incorporated into the polymer that is used to produce the web for improving the barrier properties of the web. Hydrophobic agents that may be used in accordance with the present invention include polydimethyl siloxanes and guerbet esters.

36 Claims, 1 Drawing Sheet

WATER REPELLANT MELTBLOWN WEBS AND LAMINATES

RELATED APPLICATION

The present application is based on a Provisional Application having U.S. Ser. No. 60/257,229, filed on Dec. 21, 2000.

BACKGROUND OF THE INVENTION

Non-woven fabric laminates are useful for a wide variety of applications. Such non-woven fabric laminates are useful for wipers, towels, industrial garments, medical garments, medical drapes and the like. In heavier basis weights, the laminates are used in recreational applications such as tents and as car covers.

Disposable fabric laminates have achieved especially widespread use in hospital operating rooms for drapes, gowns, towels, foot covers, sterilization wraps, and the like. Such medical fabric laminates are generally spunbond/meltblown/spunbond (SMS) laminates including nonwoven outer layers of spunbond polymers and an interior barrier layer of meltblown polymers. Examples of SMS laminates are described in U.S. Pat. No. 4,041,203 to Brock, et al., U.S. Pat. No. 4,766,029 to Brock, et al., U.S. Pat. No. 5,169,706 to Collier IV, et al., U.S. Pat. No. 5,188,885 to Timmons, et al., U.S. Pat. No. 5,464,688 to Timmons, et al., and U.S. Pat. No. 5,607,798 to Kobylivker, et al. which are all incorporated herein by reference.

Some fabric laminates, including the SMS fabric laminates, are substantially water impermeable, yet breathable allowing for water vapor transmission. For example, in an SMS laminate, the internal meltblown barrier layer is porous but still can inhibit the strikethrough of fluids or the penetration of bacteria from the outside of the fabric laminate to the inside. In order for the laminate to perform properly, it is necessary for the meltblown barrier layer to have a fiber size and a pore size distribution that assure breathability of the fabric while at the same time inhibiting strikethrough of fluids and bacteria.

In the past, those skilled in the art have attempted to design meltspun non-woven webs, such as meltblown webs, that have improved liquid repellency. For instance, in the past, fluoropolymers have been added to the polymer during formation of the web in order to improve the liquid barrier properties of the web. Such additives are disclosed in U.S. Pat. No. 5,178,932 to Perkins, et al and in U.S. Pat. No. 5,178,931 also to Perkins, et al which are both incorporated herein by reference. A need still remains, however, for methods and processes for improving the liquid repellency of meltspun webs. A need also exists for laminates containing the meltspun webs that inhibit the strikethrough of fluids.

SUMMARY OF THE INVENTION

In general, the present invention is directed to nonwoven webs made from thermoplastic polymers that have improved barrier properties, such as liquid repellency properties. The nonwoven Web can be, for instance, a meltspun web such as a meltblown web or a spunbond web. In accordance with the present invention, in order to improve the barrier properties of the web, a hydrophobic agent is incorporated into the polymer that is used to produce the web. The hydrophobic agent can be, for instance, a polydimethylsiloxane, a guerbet ester, or mixtures thereof.

The hydrophobic agent can be incorporated into the polymer in an amount less than about 10% by weight. For example, in one embodiment, the hydrophobic agent can be incorporated into the polymer in an amount from about 0.5% to about 3% by weight, and particularly in an amount of about 2% by weight.

Webs made according to the present invention exhibit improved liquid repellency properties as evidenced by hydrostatic head values, and improved blood strikethrough properties as exhibited by resistance to blood penetration values. The nonwoven webs can be used alone or can be combined into a laminate.

For example, in one embodiment of the present invention, a hydrophobic agent is combined with a polymer and formed into a meltblown web. The meltblown web is then used to form a spunbond/meltblown/spunbond laminate.

Laminates made according to the present invention can be used in many and diverse applications. For instance, the laminates can be used to form medical garments, drapes, gowns, towels, foot covers, sterilization wraps, and the like. Laminates made in accordance with the present invention can also be used to form various personal care articles, such as diapers, incontinence products, and feminine hygiene products.

Other objects, features, and aspects of the present invention are discussed in greater detail below.

DEFINITIONS

As used herein the term "meltblown fibers" means fibers of a polymeric material which are generally formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter. Thereafter, the meltblown fibers can be carried by the high velocity gas stream and are deposited on a collecting surface to form a web of randomly dispersed meltblown fibers. Such a process is disclosed, for example, in U.S. Pat. No. 3,849,241 to Butin, et al. which is incorporated herein by reference. Meltblown fibers may be continuous or discontinuous, are generally smaller than 10 microns in average diameter, and are generally tacky when deposited onto a collecting surface.

As used herein, the term "neck-bonded laminate" refers to an elastic member being bonded to a non-elastic member while the non-elastic member is extended in the machine direction creating a necked material. "Neck-bonded laminate" refers to a composite material having at least two layers in which one layer is a necked, non-elastic layer and the other layer is an elastic layer thereby creating a material that is elastic in the cross direction. Examples of neck-bonded laminates are such as those described in U.S. Pat. Nos. 5,226,992, 4,981,747, 4,965,122, and 5,336,545, all to Morman, all of which are incorporated herein by reference thereto.

As used herein the term "spunbond fibers" refers to small diameter fibers of a molecularly oriented polymeric material. Spunbond fibers may be formed by extruding a molten thermoplastic material as filaments from a plurality of fine, usually circular capillaries of a spinneret with the diameter of the extruded filaments then being rapidly reduced as by, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. Nos. 3,338,992 and 3,341,894 to Kinney, U.S. Pat. No. 3,502,763 to Hartman, U.S. Pat. No. 3,542,615 to Dobo, et al, and U.S. Pat. No. 5,382,400 to Pike, et al., which are all incorporated herein by reference. Spunbond fibers are generally not tacky when they are deposited onto a collecting surface and are generally continuous. Spunbond fibers are often about 10 microns or greater in diameter. However, fine fiber spunbond webs (having and average fiber diameter less than about 10 microns) may be achieved by various methods. The spunbond fibers can be monocomponent or multi-component fibers.

As used herein, the term "stretch-bonded laminate" refers to a composite material having at least two layers in which one layer is a non-elastic gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25 percent of its relaxed length. Such a multilayer composite elastic material may be stretched until the non-elastic layer is fully extended. One type of stretch-bonded laminate is disclosed, for example, in U.S. Pat. No. 4,720,415 to Vander Wielen, et al., which is incorporated herein by reference. Other composite elastic materials are described and disclosed in U.S. Pat. Nos. 4,789,699 to Keiffer, et al., 4,781,966 to Taylor, 4,657,802 to Morman, and 4,655,760 to Morman, et al., all of which are incorporated herein by reference thereto.

BRIEF DESCRIPTION OF THE DRAWINGS

A full and enabling disclosure of the present invention, including the best mode thereof to one of ordinary skill in the art, is set forth more particularly in the remainder of the specification, including reference to the accompanying figures in which.

Figure 1:
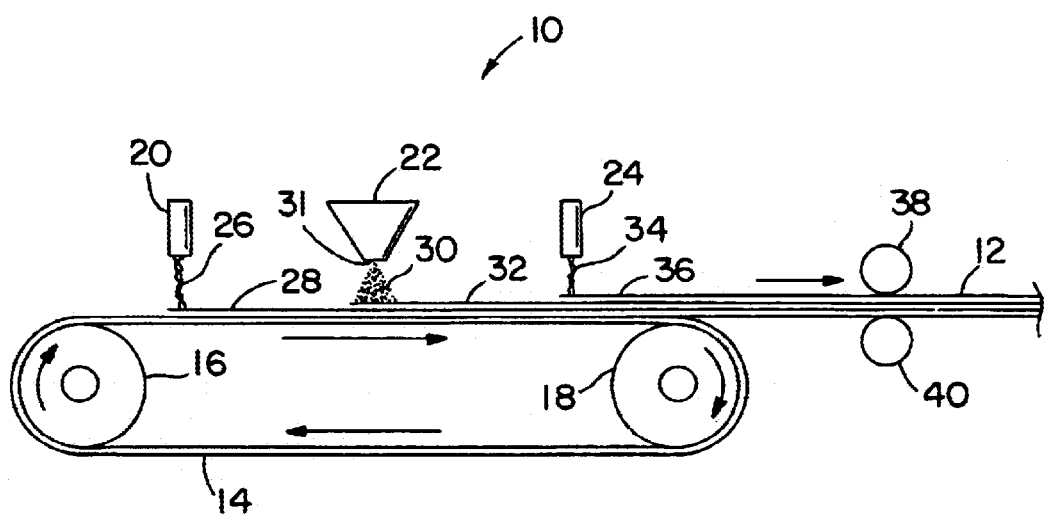
FIG. 1 is a schematic diagram of a process line for making laminates of the present invention.

Repeated use of reference characters in the present specification and drawings is intended to represent same or analogous features or elements of the present invention.

DETAILED DESCRIPTION OF PREFERRED EMBODIMENTS

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents.

In general, the present invention is directed to non-woven webs, particularly meltspun webs having improved barrier properties, such as water repellency properties. Specifically, in accordance with the present invention, a hydrophobic agent is combined with a polymer prior to or during formation of the non-woven web. For instance, the hydrophobic agent can be added to the polymer in a molten state as the polymer is being extruded into fibers or filaments, or can be precompounded with the polymer in pellet form prior to being added to an extruder. Once included in the polymer, the hydrophobic agent causes the resulting non-woven web to have a greater resistance to wetting and to the passage of fluids therethrough.

Examples of hydrophobic additives that maybe used in accordance with the present invention include siloxanes, such as polydimethylsiloxanes and guerbet esters. Examples of commercially available polydimethylsiloxanes that may be used in the present invention include LAMBENT 89, LAMBENT 88, and LAMBENT 84 which are all available from Lambent Technologies of Norcross, Ga.

In general guerbet esters are branched alcohols substituted in the 2-position with an alkyl group. Examples of guerbet esters include, by way of illustration only, 2-butyloctanol, 2-pentyinonenol, 2-hexyldecanol, 2-nonyltridecanol, 2-decyltetradecanol, and the like. Particular examples of commercially available guerbet esters that may be used in the present invention include LAMBENT CE-2000 and LAMBENT JJF-77-33C, also available from Lambent Technologies. LAMBENT CE-2000 has the following chemical structure:

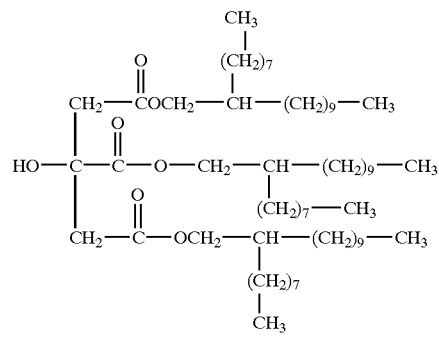

LAMBENT CE-2000 is provided as a 100% active chemical of trioctyldodecylcitrate.

The amount of the hydrophobic agent that is incorporated into a polymer in forming nonwoven webs made in accordance with the present invention can vary depending upon the particular application and the desired result. For most applications, the hydrophobic agent is present in the polymer in an amount less than 10% by weight. More particularly, the hydrophobic agent is present in the polymer in an amount less than about 5% by weight, and particuladly in an amount from about 0.5% to about 3% by weight.

In general, the hydrophobic agent can be combined with any suitable thermoplastic polymer that can be used to form nonwoven webs. Examples of thermoplastic polymers include polyolefins, polyesters, polyetheresters, and polyamides. For instance, in one embodiment, the hydrophobic additive can be combined with a polyolefin, such as polyethylene, polypropylene, and copolymers thereof.

Various different types of nonwoven webs can be formed from the thermoplastic polymers once containing the hydrophobic agent of the present invention. For example, the nonwoven web formed according to the present invention can be a meltblown web made from meltblown fibers or a spunbond web made from spunbond fibers. Nonwoven webs made in accordance with the present invention have been found to exhibit good liquid repellency properties. For instance, the webs exhibit good hydrostatic head values and good blood strikethrough properties, such as by having favorable resistance to blood penetration values.

Beside containing one or more hydrophobic agents of the present invention, the polymer used to form the nonwoven web can also contain various other additives. For example, various stabilizers can be added to the polymer, such as light stabilizers, heat stabilizers, processing aides, and additives that increase the thermal aging stability of the polymer. Further, auxiliary wetting agents, such as hexanol, antistatic agents such as a potassium alkyl phosphate, and alcohol repellants such as various fluoropolymers (e.g., DuPont Repellent 9356H) may also be present.

Once the non-woven web is formed, the web can be used alone as desired or incorporated into a laminate. For example, in one embodiment of the present invention, the non-woven web made in accordance with the present invention is a meltblown web that is incorporated into a spunbond/ meltblown/spunbond (SMS) laminate.

For exemplary purposes, one embodiment of a system for forming an SMS laminate is illustrated in FIG. 1. As shown, the system includes a forming machine generally 10 which can be used to produce an SMS fabric laminate 12 having a meltblown barrier layer 32 in accordance with the present invention. Particularly, the forming machine 10 includes an endless foraminous forming belt 14 wrapped around rollers 16 and 18 so that the belt 14 is driven in the direction shown by the arrows. The forming machine 10 has three stations, spunbond station 20, meltblown station 22, and spunbond station 24. It should be understood, however, that more than three forming stations may be utilized to build up layers of higher basis weight. Alternatively, each of the laminate layers may be formed separately, rolled, and later converted into the SMS fabric laminate off-line. In addition, the fabric laminate 12 could be formed of more than or less than three layers depending upon the requirements for the particular end use of the fabric laminate 12. For example, for recreational fabric and card cover applications, the laminate can include two inner meltblown layers.

The spunbond stations 20 and 24 are conventional extruders with spinnerets which form continuous filaments of a polymer and deposit those filaments onto the forming belt 14 in a random interlaced fashion. The spunbond stations 20 and 24 may include one or more spinneret heads depending upon the speed and process and the particular polymer being used. The nonwoven spunbond webs 28 and 36 are prepared in conventional fashion such as described in U.S. Pat. No. 3,692,618; U.S. Pat. No. 3,338,992; U.S. Pat. No. 3,341,394; U.S. Pat. No. 3,502,538; U.S. Pat. No. 3,502,763; U.S. Pat. No. 3,909,009; U.S. Pat. No. 3,542,615; U.S. Pat. No. 4,340,563; and U.S. Pat. No. 5,382,400. Other methods for forming a nonwoven web having continuous filaments of a polymer are contemplated for use with the present invention.

Spunbond materials prepared with continuous filaments generally have at least three common features. First, the polymers are continuously extruded through a spinneret to form discrete filaments. Thereafter, the filaments are drawn either mechanically or pneumatically without breaking in order to molecularly orient the polymer filaments and achieve tenacity. Lastly, the continuous filaments are deposited in a substantially random manner onto a carrier belt to form a web. Particularly, the spunbond station 20 produces spunbond filaments 26 from a fiber forming polymer. The filaments are randomly laid on the belt 14 to form a spunbond external layer 28.

The meltblown station 22 includes a die 31 which is used to form microfibers 30. The throughput of the die 31 is specified in pounds of polymer melt per inch of die width per hour (PIH). As a thermoplastic polymer exits the die 31, high pressure fluid usually air, attenuates and spreads the polymer stream to form microfibers 30. The microfibers 30 are randomly deposited on the top of the spunbond layer 28 and form a meltblown layer 32. In one embodiment of the present invention, a hydrophobic agent is combined with the thermoplastic polymer that is used to form meltblown layer 32.

The meltblown station 22 produces fine fibers 30 from a fiber forming polymer. The fibers 30 are randomly deposited on top of spunbond layer 28 to form a meltblown internal layer 32. For an SMS medical fabric laminate, for example, the meltblown barrier layer 32 has a basis weight of from about 0.2 osy (ounces per square yard) to about 0.8 osy, and particularly from about 0.6 osy to about 0.5 osy.

After the internal layer 32 has been deposited by the meltblown station 22 onto layer 28, spunbond station 24 produces spunbond filaments 34 which are deposited in random orientation on top of the meltblown layer 32 to produce external spunbond layer 36. For an SMS medical fabric laminate, for example, the layers 28 and 36 each have a basis weight of from about 0.2 osy to about 2.0 osy, and particularly from about 0.3 osy to about 1.2 osy.

Figure 2:
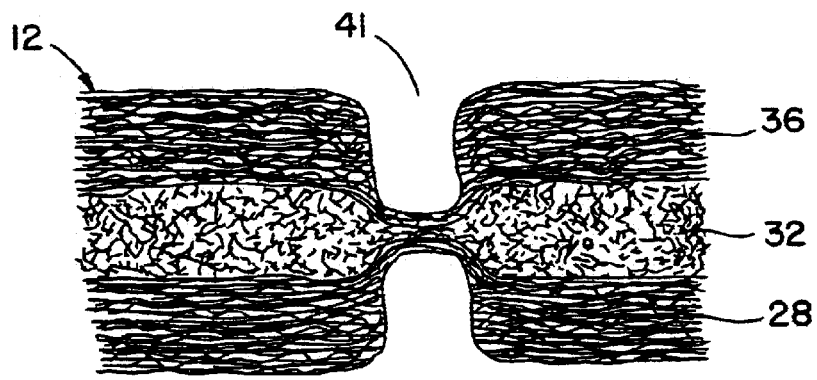
FIG. 2 is a cross-sectional view of one embodiment of a laminate made in accordance with the present invention.

The resulting SMS fabric laminate web 12 as shown in FIG. 2 is then fed through bonding rolls 38 and 40. The surfaces of the bonding rolls 38 and 40 are provided with a raised pattern such as spots or grids. The bonding rolls are heated to the softening temperature of the polymer used to form the layers of the web 12. As the web 12 passes between the heated bonding rolls 38 and 40, the material is compressed and heated by the bonding rolls in accordance with the pattern on the rolls to create a pattern of discrete areas, such as 41 shown in FIG. 2, which areas are bonded from layer to layer and are bonded with respect to the particular filaments and/or fibers within each layer. Such discrete area or spot bonding is well known in the art and can be carried out as described by means of heated rolls or by means of ultrasonic heating of the web 12 to produce discrete area thermally bonded filaments, fibers, and layers. In one embodiment, the fibers of the meltblown layer of the fabric laminate are fused within the bond areas while the filaments of the spunbond layers retain their integrity in order to achieve good strength characteristics.

Besides being used to form SMS laminates as described above, it is believed that nonwoven webs made in accordance with the present invention can also be used to form various other laminates. For example, meltblown webs made in accordance with the present invention can also be used to form neckbonded laminates and stretchbonded laminates. It should also be understood that the hydrophobic additives of the present invention can be incorporated into a single layer or into every layer of the laminate.

EXAMPLE

The following example was performed in order to compare meltspun webs incorporating a hydrophobic agent of the present invention with webs not containing the hydrophobic agent.

Meltblown nonwoven webs were prepared. All webs had a basis weight of about 1.5 ounces per square yard. All of the fabrics were topically treated with a hexanol auxiliary wetting agent. The hexanol was applied to the web in an aqueous solution containing 0.3% by weight hexanol. After being applied to the web, substantially all of the hexanol evaporated upon drying. Some of the fabrics were additionally treated with a topical fluoropolymer for alcohol repellency (DuPont® Repellent 9356H), and a potassium alkyl phosphate antistatic additive (Quadrastat PIBK). The fluoropolymer and the antistatic additive were added to the web at an add-on level of about 0.36% by weight for the fluoropolymer and at about 0.22% by weight for the antistatic additive.

In addition, the nonwoven webs contained the hydrophobic additives of the present invention. The hydrophobic additives were compounded into polypropylene pellets containing 10% by weight of the hydrophobic additive. The compounded pellets were combined with other polypropylene pellets such that the hydrophobic additive was added at a 2% by weight total add-on level. The combined pellets were fed to a meltblown die for forming the meltblown webs.

Two types of hydrophobic additives were investigated, polydimethylsiloxanes and guerbet esters, all produced by Lambent Technologies of Norcross, Ga. The polydimethylsiloxanes investigated included Lambent 89 (L89), Lambent 88 (L88), and Lambent 84 (L84). The guerbet esters investigated included Lambent CE-2000 and Lambent JJF-77-33C.

The testing procedures are described as follows:

Hydrohead: A measure of the liquid barrier properties of a fabric is the hydrohead test. The hydrohead test determines the height of water (in centimeters) which the fabric will support before a predetermined amount of liquid passes through. A fabric with a higher hydrohead reading indicates it has a greater barrier to liquid penetration than a fabric with a lower hydrohead. The hydrohead test is performed according to Federal Test Standard 191A, Method 5514. Results are reported in centimeters with standard deviations.

Resistance to Blood Penetration (RBP): The blood strikethrough or resistance to blood penetration of a fabric is a measure of the amount of blood which penetrates the fabric at a particular pressure. The blood strikethrough is performed by weighing a blotter placed next to the fabric before and after the test which consists of applying 1 pound per square inch gauge (psig) pressure to the side of the fabric away from the blotter, which side has blood thereon. The pressure is ramped up over approximately 10 seconds and removed when it reaches 1 psig. The difference in the weight of the blotter before and after the test in grams represents the amount of blood which has penetrated the fabric. Results are reported as a percentage of the change of weight of the blotter.

Charge Acceptance/Static Decay: This test determines the electrostatic properties of a material by measuring the time required for dissipating a charge from the surface of the material. Except as specifically noted, this test is performed in accord with INDA Standard Test Methods: IST 40.2 (95). Generally described, a 3.5 inch by 6.5 inch specimen is conditioned in a 50% RH environment, including removal of any existing charge. The specimen is then placed in electrostatic decay testing equipment and charged to a predetermined voltage. Once the specimen has accepted the charge (reported as charge acceptance), the charging voltage is removed and the electrodes grounded. The time was recorded for the sample to have a 50% decay. The test was then repeated to measure a 90% decay. The time was recorded.

Table 1 displays the testing results for meltblown fabrics without an added topical fluoropolymer and antistatic additive.

TABLE 1

| Sample # | Hydrophobic additive | Hydrohead (cm) | RBP (%) | Charge Acceptance Kv | 50% Static decay (sec) | 90% Static decay (sec) |
|---|---|---|---|---|---|---|
| 1 | None | 52.1 | 1.88 | 5 | 0.86 | 0.96 |
| 2 | L89 | 71.8 | 1.89 | .750 | 0.02 | 0.13 |
| 3 | L88 | 67.1 | 1.49 | .416 | 0.02 | 2.01 |
| 4 | L84 | 54.9 | 2.01 | .250 | 0.02 | 0.015 |
| 5 | CE-2000 | 73.6 | 1.56 | 5K | 0.16 | 0.17 |
| 6 | JJF-77-33 | 68.6 | 1.91 | 5K | 0.16 | 0.15 |

Table 2 displays the testing results for meltblown fabrics which include an added topical fluoropolymer and antistatic additive.

TABLE 2

| Sample # | phobic additive | Hydrohead | RBP | Charge Acceptance Kv | 50% Static decay (sec) | 90% Static decay (sec) |
|---|---|---|---|---|---|---|
| 7 | None | 55.5 | 1.61 | 5 | 0.33 | 0.27 |
| 8 | JJF-77-33 | 77.8 | 1.76 | 5 | 0.09 | 0.10 |
| 9 | CE-2000 | 74.6 | 1.33 | 5 | 0.03 | 0.02 |
| 10 | L84 | 73.2 | 1.10 | .250 | 0.01 | 0.02 |
| 11 | L88 | 67.5 | 1.08 | .166 | 0.01 | 0.02 |
| 12 | L89 | 74.2 | 1.68 | 1.3 | >60 | 0.03 |

As shown above, meltblown webs treated in accordance with the present invention generally have improved liquid repellency properties.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A meltspun web having improved liquid repellency properties, the meltspun web comprising a thermoplastic polymer and a hydrophobic agent, the hydrophobic agent being incorporated into the thermoplastic polymer, the hydrophobic agent comprising a guerbet ester.

2. A meltspun web as defined in claim 1, wherein the guerbet ester comprises trioctyldodecylcitrate.

3. A meltspun web as defined in claim 1, wherein the thermoplastic polymer is a polyolefin, a polyester, a polyetherester, or a polyamide.

4. A meltspun web as defined in claim 1, wherein the thermoplastic polymer is polypropylene or polyethylene.

5. A meltspun web as defined in claim 1, wherein the web is a meltblown web.

6. A meltspun web as defined in claim 1, wherein the web is a spunbond web.

7. A meltspun web as defined in claim 1, wherein the meltspun web further comprises a fluoropolymer topically applied to the web.

8. A meltspun web as defined in claim 1, wherein the web has a basis weight of up to about 2 osy.

9. A meltspun web as defined in claim 1, wherein the web has a hydrohead of at least 60 cm.

10. A meltspun web as defined in claim, 1, wherein the web has a resistance to blood penetration of less than about 1.7%.

11. A meltspun web as defined in claim 1, wherein the hydrophobic agent is incorporated into the thermoplastic polymer in an amount up to about 10% by weight.

12. A meltspun web as defined in claim 1, wherein the hydrophobic agent is incorporated into the thermoplastic polymer in an amount from about 0.5% to about 5% by weight.

13. An absorbent product incorporating the meltspun web defined in claim 1.

14. A laminate comprising at least a first layer bonded to a second layer, the first layer comprising a meltspun web having improved liquid repellency properties, the meltspun web comprising a thermoplastic polymer and a hydrophobic agent, the hydrophobic agent being incorporated into the thermoplastic polymer, the hydrophobic agent comprising a guerbet ester.

15. A laminate as defined in claim 14, wherein the guerbet ester comprises trioctyldodecylcitrate.

16. A laminate as defined in claim 14, wherein the thermoplastic polymer is a polyolefin, a polyester, a polyetherester, or a polyamide.

17. A laminate as defined in claim 14, wherein the thermoplastic polymer is polypropylene or polyethylene.

18. A laminate as defined in claim 14, wherein the meltspun web is a meltblown web.

19. A laminate as defined in claim 18, wherein the second layer comprises an outer spunbond layer and wherein the laminate includes a third layer comprising an outer spunbond layer, the meltblown layer being positioned in between the two outer spunbond layers.

20. A laminate as defined in claim 14, wherein the meltspun web is a spunbond web.

21. A laminate as defined in claim 14, wherein the meltspun web further comprises a fluoropolymer, topically applied to the web.

22. A laminate as defined in claim 14, wherein the meltspun web has a basis weight of up to about 2 osy.

23. A laminate as defined in claim 14, wherein the meltspun web has a hydrohead of at least 60 cm.

24. A laminate as defined in claim 14, wherein the meltspun web has a resistance to blood penetration of less than about 1.7%.

25. A laminate as defined in claim 14, wherein the hydrophobic agent is incorporated into the thermoplastic polymer in an amount up to about 10% by weight.

26. A laminate as defined in claim 14, wherein the hydrophobic agent is incorporated into the thermoplastic polymer in an amount from about 0.5% to about 5% by weight.

27. A laminate as defined in claim 14, wherein the layers are thermally bonded together.

28. A medical garment incorporating the laminate defined in claim 14.

29. A shoe covering incorporating the laminate defined in claim 14.

30. A personal care article incorporating the laminate defined in claim 14.

31. A drape incorporating the laminate defined in claim 14.

32. A laminate comprising a first layer bonded to a second layer, the first layer comprising a meltblown web made from a thermoplastic polymer, the thermoplastic polymer comprising polyethylene or polypropylene, the thermoplastic polymer incorporating a hydrophobic agent, the hydrophobic agent comprising a guerbet esters, the hydrophobic agent being present in the thermoplastic polymer in an amount from about 0.5% to about 5% by weight, the meltblown web having a basis weight of up to about 2 osy.

33. A laminate as defined in claim 32, wherein the second layer comprises a spunbound web.

34. A laminate as defined in claim 33, wherein the laminate further comprises a third layer comprising a spunbond web, the meltblown web being located between the two spunbond webs.

35. A laminate as defined in claim 34, wherein the layers are thermally bonded together.

36. A laminate as defined in claim 32, wherein the guerbet ester comprises trioctyldodecylcitrate.

* * * * *